United States Patent
Barr et al.

(10) Patent No.: US 6,812,254 B1
(45) Date of Patent: Nov. 2, 2004

(54) PAIN RELIEVER AND METHOD OF USE

(75) Inventors: Teresa Leigh Barr, Port Townsend, WA (US); Stephen D. Holt, Little Rock, AR (US)

(73) Assignee: Medical Merchandising Inc., Little Rock, AR (US)

( * ) Notice: Subject to any disclaimer, the term of this patent is extended or adjusted under 35 U.S.C. 154(b) by 0 days.

(21) Appl. No.: 09/534,953

(22) Filed: Mar. 24, 2000

Related U.S. Application Data

(63) Continuation-in-part of application No. 09/408,740, filed on Sep. 29, 1999.

(51) Int. Cl.$^7$ .......................... A61K 31/16; A61K 31/74
(52) U.S. Cl. ....................... 514/627; 514/825; 514/887; 424/77; 424/78.05
(58) Field of Search ................................. 514/627, 358

(56) References Cited

U.S. PATENT DOCUMENTS

| | | | | |
|---|---|---|---|---|
| 4,546,112 A | * | 10/1985 | LaHann et al. | |
| 4,963,591 A | * | 10/1990 | Fourman et al. | |
| 5,856,361 A | * | 1/1999 | Holt et al. | 514/627 |
| 6,074,652 A | * | 6/2000 | Ishiwatari et al. | |
| 6,197,823 B1 | * | 3/2001 | Barr et al. | 514/627 |
| 6,221,915 B1 | * | 4/2001 | McCleane | |
| 6,248,763 B1 | * | 6/2001 | Scivoletto | 514/356 |
| 6,348,501 B1 | * | 2/2002 | Holt et al. | 514/627 |

* cited by examiner

*Primary Examiner*—Sreeni Padmanabhan
*Assistant Examiner*—Jennifer Kim
(74) *Attorney, Agent, or Firm*—Wendy K. Buskop; Stephen D. Carver

(57) ABSTRACT

A composition containing capsaicin together with other ingredients to neutralize the discomfort resulting from the application of capsaicin to the ski enabling treatment of many types of discomforts, including arthritis pain, neuropathy, post surgical scarring, hemorrhoid pain and itching, and pruritis without the discomfort normally associated with the topical application of capsaicin.

33 Claims, No Drawings

PAIN RELIEVER AND METHOD OF USE

This is a continuation in part application of Ser. No. 09/408,740 filed Sep. 29, 1999.

BACKGROUND OF THE INVENTION

In one aspect, this invention relates to a composition of matter useful for treating bodily pains and discomforts. In another aspect, this invention relates to a method for treating bodily pains and discomforts. In yet another aspect, this invention relates to formulating a pain and discomfort reliever.

Arthritis is medically termed as an inflammation of a joint or joints and is one of a number of diseases and disorders of the skeleton and body system. Arthritis arises from many causes, some well-defined, some still unknown, and it is treated in many different ways. There are two common types, the first of which is inflammatory, of which rheumatoid arthritis is the most commonly acknowledged and a non-inflammatory, second type, most commonly represented by degenerative joint disease, or wear and tear arthritis. Inflammatory arthritis is a disease not of the joints alone but of the whole bodily system, in particular, the connective tissues of the body. It is an auto-immmune disease, where the body's immune system attacks its own host (i.e. itself) and produces inflamation. Degenerative joint disease is a chronic joint disease, often occurring in more elderly people. In both cases many manifestations are similar. The joints, whether singly or in multiples, are affected. The joints may become swollen, warm, deformed, gnarled, and in many instances present grotesque deformities. In many cases it also affects the adjacent muscles and tendons, as well as other connective tissues of the body. The primary disease produces symptomatic swelling, pain and stiffness.

Various new and old drugs have been developed for the treatment of arthritis, anywhere from non-steroidal anti-inflammatory drugs to cortisone. Many of these systemic drugs have dangerous side effects. Their dosage must be carefully prescribed and administered under controlled conditions and circumstances to avoid unpleasant and dangerous side effects.

Several topical agents (creams, ointments, liniments, lotions and the like) have been utilized for the relief of the pains and aches of arthritis. Most of these have provided a little, but only temporary, relief to persons suffering from pain. Many combinations of varying ointments, creams, aqueous solutions, liniments and the like for the treatment of arthritis are known. The most efficacious of these contains as its active ingredient the vegetable products derived from the seed and pods of the capsicum plant, commonly known as red pepper. Capsicum-derived ointment is devised for external application to the affected area of the body by applying to the area adjacent to the muscle, joint or tendon and rubbing it into the skin. The active ingredient is capsaicin. With initial as well as persistent application, capsaicin is effective to relieve the aches and pains of various muscle or skeletal origin, such as arthritis, muscle strains, tendonitis, bursitis and soft tissue diseases.

Capsacin is also effective to relieve the various musculoskeletal pains, itching, neuropathic pains, dysesthesias caused by shingles, post herpetic neuralgia, post mastectomy pain, and peripheral neuropathies. It is further commonly prescribed to reduce the pain of neuropathies produced by diabetes (burning pain, discomfort, often at night) and other diseases that are neuropathic in origin including the discomfort and odd sensations of shingles (post herpetic neuralgia, which can be extremely painful), as well as dysesthesias that can occur with thoracotomies and post surgical scars.

Unfortunately, although capsaicin is often the most effective agent available, the active ingredient is a potent skin irritant, producing a burning, uncomfortable sensation to the skin. Although prescribed frequently, it is used to only a limited extent due to this unpleasant side effect.

The burning side effect has also discouraged the use of capsaicin to treat other types of discomfort, such as pruritus or itching. Pruritus or itching can be caused by many stimuli, such as poison ivy, hemorrhoids, or athlete's foot. The unpleasant side effects of capsaicin have discouraged its use to treat such types of discomfort Also, the burning that occurs when the skin is exposed to sunlight that has been treated with capsaicin or exposed to water has discouraged the use of capsaicin.

A capsaicin based pain reliever which does not irritate the skin or cause a burning discomfort even when exposed to water and sunlight, would be extremely desirable and acceptable to patients and people in general who are experiencing the types of pain or discomfort outlined above.

Prior attempts to produce such an invention can be seen in U.S. Pat. No. 5,134,166 and U.S. Pat. No. 4,997,853, which use anesthetics in association with capsaicin, effectively numbing sites. The present invention does not attempt to numb the site, but instead permits continued use of the hand or foot, with sensory input remaining in tact, rather than simply blocking all sensory input to the area while warming with capsaicin.

OBJECTS OF THE INVENTION

It is an object of this invention to provide a capsaicin based pain reliever, which can be applied transdermally.

It is another object of this invention to provide a method for formulating a no-burn capsaicin-based pain reliever for tendons, muscles and joints in which the capsaicin is fully functional, one, which provides analgesic and anesthetic properties.

Another object of the invention is to provide a topical formulation, which can be used for blows and strains to muscles.

SUMMARY OF THE INVENTION

In accordance with one aspect of the invention, there is provided a composition comprising a carrier, capsaicin, an encapsulation agent, an ester of amino acid and a light-diffusing compound.

In accordance with another aspect of the invention, there is provided a method for treating a victim of pain or discomfort. The treatment comprises applying the above-described composition topically to the skin of the victim near an area affected by the pain or discomfort.

In accordance with a further aspect of the invention, there is provided a method for making a composition useful for topical application to treat pain or discomfort. The method is carried out by mixing a carrier to form an aqueous solution, adding an encapsulation agent to reduce burning of the capsaicin, adding an amount of esters of amino acids and finally adding a light refractive element having an ability to stop secondary burning effect by the capsaicin due to the suns rays. The resulting aqueous solution preferably has a cream-like viscosity.

DETAILED DESCRIPTION OF THE PREFERRED EMBODIMENTS

The present invention has been devised to use in nerve damage treatment such as after a patient has experienced shingles. Additionally, the present invention is a composition for the treatment of the following conditions; arthritis, tendonitis, bursitis, myositis myalgia and arthralgia.

Capsaicin is trans-8-methyl-N-vanillyl-5 none amide, a naturally occurring alkyl vanillylamide, a type of capsaicinoid. It is found in high concentration in fruit of plants of the Capsicum genus. The chili pepper, red pepper and paprika are all species of Capsicum. All hot papers contain capsaicinoids. Capsaicinoids are natural materials, which produce a burning sensation in the mouth. Capsicum has recently been officially defined in the USP 23 where it is defined as the dried ripe fruit of Capsicum frutescens Linne or Capsicum annum Linne.

There are two main capsaicinoids, capsaicin and dihydrocapsaicin and three minor capsaicinoids, nordihydrocapsaicin, homocapsaicin and homodihydrocapsaicin. All capsaicinoids are considered usable within the scope of this invention.

Capsicum is the dry powder obtained by grinding up the fruits of these plants. Capsicum oleoresin (or capsaicin oleoresin) is the liquid concentrate extracted from the dry powder. Capsaicin, a white crystalline material, is obtained from the liquid concentrate.

The composition of the invention comprises capsaicin as a first active ingredient and at least one-second active ingredient acting as an analgesic to reduce the sensation of capsaicin induced skin irritation. The ingredients are contained in a carrier fluid. The genus capsicum is a member of a large tropical family solanaceae. There are numerous Species, of which Capsicum annur, Capsicum Chinese and Capsicum frutescens are closely related. Capsicum frutescens is also known as Cayenne Pepper, Chili Pepper, Pimento Tabasco Pepper and Tabasco-sauce pepper.

Capsaicin (N-yanillyl-8-methyl-6-(E)-none amide) is the most pungent of the capsaicinoids. It is very soluble in fats, oils and alcohols. Capsicum also contains a red coloring matter, oleic acid, palmitic acid and stearic acid.

Capsicum frutescens extract can be obtained from Bio-Botanica, Inc. of Hauppauge, N.Y. and appears as a viscous fluid, having a sallow yellow color, a caustic and pungent aroma, and is soluble in ethanol.

Capsicum is a powerfull local stimulant. It is strongly rubifacient acting without vesication.

Generally speaking, the composition will contain in the range of 0.00125% to 1% by weight of capsaicin. However, compositions containing less than 0.00125% by weight, down to 0.0001% of capsaicin will provide a therapeutic, effect. Even trace concentrations of capsaicin (such as 0.00001% by weight) will provide a minute therapeutic effect. Compositions containing more than 1% by weight of capsaicin will also provide a therapeutic effect, up to 62% by weight capsaicin, except that the burning side effect will increase in proportion to the increase percentage of capsaicin. Compositions containing 0.025% to 20% by weight of capsaicin could be used. Compositions of 0.025 to 2% by weight are considered usable as well. Even so, compositions containing in the range of 0.025% to 0.25% by weight of capsaicin are preferred because they are narrowly encompassed within current FDA guidelines. However, the FDA guidelines were developed at a time when there was not an effective method for relieving the discomfort generated by capsaicin. The present invention provides a method to increase the amount of capsaicin that can be administered comfortably.

In the present invention, capsaicin is mixed with a carrier fluid. Preferably, the carrier fluid is water-based and forms an aqueous solution containing the ingredients. However, the carrier may be a fluid such as an oil based carrier, a fat based carrier, a fatty alcohol based carrier or combination of these.

Additional irritant is added to the capsaicin and carrier. Histidines, such as a histamine dihydrocholride are considered usable in the scope of the present invention to create vasodilatation, and act as a second irritant. Adding the second irritant produces an analgesic effect and does not numb the site, like an anesthetic or depress cutaneous sensory receptors. It is possible to add more than one histidine to achieve the analgesic reaction. Instead, it has a topical counter irritant effect by stimulating cutaneous sensory receptors, see, Federal Register, Vol 48, No. 27, Tuesday Feb. 8, 1983, pages 5367 et. seq., Specifically, amine and caine type local anesthetics, such as benzocaine and lidocaine, act differently as anesthetics not producing an analgesic effect which is achieved by adding an additional irritant, such as a histamine hydrochloride or most preferably a histamine dihydrochloride. If a histamine dihydrochloride is used, it is preferred to use a starting composition of 98% histamine, although compositions in the range of 96–99% histamine will be usable as well.

Any one of the following histidines, or combinations thereof, are considered usable in this invention, L-histidines, histamine dihydrocholoride, DL-histidine, D-histidine hydrochloride monohydrate, L-histidine hydrochloride monohydrate, L-histidine methyl ester dihydrochloride, L-histidinol dihydrochloride.

When histidines are used in the invention, it is preferred that the weight percent of the material is between 0.001% and about 1.0 wt. %. However in the most preferred embodiment, 0.025 and 0.10 wt. % are contemplated.

Other histidines are considered usable within the scope of this invention, as well as the second irritant. It is possible though, that the invention will work well with out the second irritant.

The novel composition further comprises an encapsulation agent such as colloidal oatmeal, hydrogenated lecithin, dipotassium glycyrrhizinate or other similar encapsulation agents, or even combinations of these agents with the capsaicin and second irritant. The colloidal oatmeal has intrinsic SFP, natural sunscreen capability. In addition, the colloidal oatmeal can serve to encapsulate the capsaicin to reduce the inflammation effect the capsaicin has on the skin, while still enabling the capsaicin to work effectively. Typically, 0.35 wt. % colloidal oatmeal is used in this invention, although any amount between 0.20 and up to about 0.60 wt. percent can be used. The colloidal oatmeal works within the scope of this invention because it contains hydrophilic colloids. These colloids help to provide a protective barrier on the skin to control inflammation In addition, histidines, such as L-histidines, are present in colloid oatmeal. Histidines can be present in the oats in weight percents up to 3% of the total amino acids in the oats. The invention has found that using the colloidal oats enhance, synergistically the histamine dichlorohydride effect, when histamine dichlorobydride is used.

The dipotassium glycyrrhizinate is prepared from finely cut licorice root extracted with water. Ethanol is then added to this extract and the precipitate is separated after sedimentation. Inorganic acid is added to the filtrate, and the precipitating sediment is filtered. After neutralization with water, it is dissolved in a potassium hydroxide solution and evaporated until dry. The residue, is recrystallized in media such as acetic acid or ethanol to obtain monopotassium glycyrrhizinate. The product is faintly yellow without an order and sweet in taste. Typically this product can be acquired from Barnet Products Corp. of Englewood Cliffs, N.J.

Hydrogenated lecithin is available from Barnet Products Corporation, as well. It is an emulsifier and stabilizer for solutions. In addition, it is used to reduce inflammation on the skin. The unique lecithin will synergistically react with the dipotassium glycyrrhizinate to enhance the effect of the dipotassium glycyrrhizinate on encapsulation of the capsaicin. Additionally, the lecithin is used to reduce irritation, which differs from inflammation. Inflamed skin is red and hot, irritated skin is itchy without necessarily being inflamed and red.

Esters of amino acids are next added to the formulation. Esters of amino acids usable in the scope of this invention are preferably lauryl menthyl esters of amino acids. In the most preferred embodiment, the esters of amino acids arm menthyl lauryl pidolate. This ester is comprised of menthyl as well as pidolic acid and lauric alcohol. This component [[.]]has no odor. Typically, 0.1–1.0 wt. % is used in this compound il order to create the necessary analgesic effect. The active element in this component is menthol, which acts as an analgesic. It is considered within the scope of the present invention to use enough menthyl lauryl pidolate to attain between 0.1 and 16 wt. % menthol in the formulation. Additionally, polysorbate and benzyl alcohol can be added to the formulations. It is contemplated that the amount added can be in weight percents based on the total formula of about 0.18% by weight. The polysorbate is believed to add the feature of a emulsifier & stabilizer, The benzyl alcohol can be added to the formulation to add the feature of keeping the skin from burning and acting as a solvent for colloidal oats as well as a preservative.

The unique formulation is a topically (externally) applied formulation which has three simultaneous effects, analgesic, anesthetic and antipruritic effects, by (1) depressing cutaneous sensory receptors to relieve pain and (2) stimulating cutaneous sensory receptors using a topical counter irritant.

It is the combination of analgesic and anesthetic which make this invention unique.

Further, a light scattering compound is added to the formulation. Light scattering compounds can be any compounds, which have the ability to scatter light, such as by using particles having a diameter up to about 100 microns and more preferably between 30–60 microns.

Titanium dioxide is considered the best light scattering element for the present invention. Titanium dioxides usable within the scope of the present invention are preferably fine particle or pigmentary titanium dioxides available from Solaveil, of Durhamn, England. Any of the Solaviel TiO$_2$ products for cosmetic use can be used. All will reflects ultraviolet and provide broad UVB light protection, effectively scattering the light rays. In a preferred embodiment, the TiO$_2$ can provide a complete block of sunlight, and when mixed with the colloidal oatmeal, the light waves can be refracted and the skin protected from burning from the light.

Other than titanium dioxides, other components can be used for the light scattering purpose. For example, octyl dodecyl neopentanoate can be used for light scattering. Bernell Chemical sells these compounds. Zinc oxide can be used as light scattering component, which also has the advantage of being anti-itch, or anti-pruritic effect.

Also, benezophenones, methoxycinnamate, para amino benzoic acid and combinations thereof can be used. It is also within the scope of the present invention, to add component onto the surface of the titanium dioxide to further enhance the effect of the titanium dioxide. In particular, aluminum stearate and aluminum oxide can be additionally used with the titanium dioxide for light scattering.

The titanium dioxide, with or without the aluminum is typically dispersed in caprylic/capric triglyceride, causing this component to contain approximately 50% by weight of solids.

It should be noted that other additives may be used in the present invention such as xanthum gum, myristal myristate and other stearates for coagulation of the compound.

Additional components can be added to the formulation, such as "lavender flower oil" or lavender oil, and a "bergaptene-free" bergamot oil or bergamot extract is expected to be beneficial in that the lavender provides a muscle relaxant characteristic and the bergamot oil provides help with acne, fevers, herpes, and diabetic neuropathy.

Also, for enhancing the composition, other elements may be added to the composition. The following are contemplated:

1. Arnica montana
2. Hypericum perforatum (known as St. John's Wort)
3. Aloe barbadensis gel
4. Citric acid to adjust the pH of the compound
5. Propylene glycol with menthyl and propyl parabens as preservatives
6. A chealating agent to keep the product from separating, such as edetatedisodium
7. Triethanolamine hydrochloride which acts as a reagent
8. Other preservatives Still others considered usable in the present invention are phenoxy ethanol, ethyl paraben, and butyl paraben as preservatives, or in the preservative system. Other ingredients such as inositol, menthyl paraben, propyl paraben, hydtoxy ethyl cellulose can be used therein, for formulations which are gels rather than creams. Carbomer 940 can be used to make the formula into a gel rather than a cream.

Xanthum gum can be added to the invention to provide a higher density compound, and act as a thickening, agent. Other elements, such as licorice extract, glyceryl polymethacrytate and hydroxypropyl cellulose can be used in various formulations of the basic invention.

A suspension agent can be added to the formula of the present invention. Alkyl benzoate is considered usable within the scope of the present invention, and helps to suspend the particle size of components used in this system.

Deionized water is an excellent aqueous carrier for the present invention.

The present invention is fast acting and long acting due to the menthol present in the compositions. The uses of the invention are contemplated for post perpetic neuralgia, and scar conditions after surgery, such as for treating the scars from a mastectomy. Also, the preset invention is considered usably for victims of neuropathy, such as diabetes with neuropathy.

In the method of the invention, a victim of pain or discomfort is treated by applying the above-described composition topically to the skin of the victim near an area affected by the pain or discomfort. The types of pain or discomfort to which the invention may be applied include those discussed in the background of the invention. Generally speaking, the inventive composition, preferably in cream, pigment and lotion form, is applied to the selected area, such as a joint, and rubbed in. The amount applied is not critical. Generally, it should be applied in an amount that is sufficient to wet the area of application. Usually, the amount used will be in the range of from about 0.3 to about 3

For the treatment of pruritus or itching, the application of the composition can be repeated as required to control the discomfort. When the preferred composition of the invention is applied, it provides near immediate relief from the itching caused by poison ivy or hemorrhoids, without a burning sensation. The relief lasts for several hours. It is surprising that a capsaicin-based composition would be useful for the treatment of such discomfort. To enhance the antipruritic effect, additional compounds can be added to the formulation. These components can be menthyl sulphonyl methane, sodium bicarbonate, calamine, allatoin, kaolin, cortisone, anti-inflammatory steroids, anti-allergic steroids, and combinations or derivatives thereof.

For best results in the treatment of arthritis, the treatment should be repeated several times per day, such as in the range of 2 to 8 times per day, preferably 3-5 times per day, and continued for several days. Surprisingly, most patients do not experience the burning discomfort heretofore known as a very common side effect of topical capsaicin application.

It is contemplated to be within the scope of the present invention to use this formulation for a gel, a cream, an opaque cream, a spray using propellants, such as butyl propellants, and a liquid or lotion, such as a roll on.

It is even contemplated that the present invention could be used as a patch for treatment as well. Propellant for the spray on composition contemplated as usable herein can be selected from the group butane, propane, isobutane, and combinations thereof. A foam version of the formulation, additionally using a propellant and a surfactant is considered within the scope of the present invention. A preferred surfactant is a member of the group of amine oxides. The most preferred surfactant is alkyl dimenthyl amine oxide.

The forgoing is a description of the composition and method of use of three embodiments of the invention. The scope of the invention is considered to include the described embodiment together with others obvious to those skilled in the art.

COMPOSITION EXAMPLE

The resulting composition made in accordance with one embodiment of the invention contains the following ingredients.

| Ingredient | wt. % |
|---|---|
| deionized water | Q.S. |
| triethanolamine hydrochloride | 0.05 |
| edetate disodium | 0.05 |
| methyl paraben | 0.03 |
| propyl paraben | 0.02 |
| lavender oil | 4.0 |
| capsaicin | 0.0133 |
| Arnica montana extract | 1.0% |
| Aloe barbadensis gel | 15.0% |
| colloidal oatmeal | 12.0% |
| hydrogenated lecithin | 0.05% |
| stearates | 10.0% |
| myristal myristate | 1.0% |
| polysorbate | 20.0% |
| titanium dioxide solution (50% solids) | 10.0% |
| benzyl alcohol | 8% |

In addition to the above ingredients, up to 10% by weight of the formulation can be carbopol. Additionally hydroxypropyl cellulose can be used up to 5% or hydroxmnethyl cellulose can be used in up to the same amount. Also, a menthyl sulfonyl methane, from 10–15% by weight of the entire formulation can be used to assist with pain in the tendons and the joints.

Second Preferred Embodiment

In an alternative embodiment, the following elements are preferred:

Aloe vera gel
Arnica Montana
Benzly alcohol
Caprylic-capric triglyceride
Titanium dioxide
Alumina
Polyhydroxy stearate
Lavender oil
Cetyl alcohol
Colloidal oatmeal
Glyceryl monostearate
Lecithin
Myristal myristate
PEG 100 stearate
Phenoxyethanol
Methyl paraben
Ethylparaben
Propylparaben
Butylparaben
Polysorbate 80
Tetrasodium EDTA
Triethanolimine
Transdermal Application The present invention related to a composition which can be used in a form which has absorption rates which permit transdermal application to a skin and an ability to penetrate past chemical barriers in transcutaneous manners for quick absorption into the blood stream.

Polysorbate can be added to the formula to add body to the composition and to act as a emulsifier and stabilizer to improve the shelf life of the composition.

What is claimed is:

1. A composition comprising:
   a carrier;
   an encapsulated capsaicin;
   an encapsulation agent for the capsaicin, wherein the encapsulation agent consists of a colloidal oatmeal or a dipotassium glycyrrhizinate;
   lauryl menthyl esters of amino acid;
   a light scattering element having a particle size up to 100 nm; and
   an oil based alcohol.

2. The composition of claim 1, wherein the oil based alcohol is selected from the group, benzyl alcohol, butylene glycol, propylene glycol alcohol benzoate, benzene methanol and a hydroxy toluene.

3. A composition comprising:
   a carrier;
   an encapsulated capsaicin;
   an encapsulation agent for the capsaicin, wherein the encapsulation agent consists of a colloidal oatmeal or a dipotassium glycyrrhizinate;
   lauryl menthyl esters of amino acid;
   a light scattering element having a particle size up to 100 nm; and
   an emulsifying agent.

4. The composition of claim 3, wherein the emulsifying agent is selected from the group comprising: polysorbitol, soibitol, glycerine and corn syrup.

5. The composition of claim 1, wherein the carrier is selected from the group comprising: aqueous carriers, oil based carriers, fat based carriers, and fatty alcohol based carriers, corn oil, edible oil, white oil, liquid petrolatum or combinations thereof.

6. The composition of claim 1, further comprising at least one histidine.

7. The composition of claim 6, wherein the at least one histidine is a histamine hydrochloride.

8. The composition as in claim 7, wherein said histamine hydrochloride is a dihydrochloride.

9. The composition as in claim 7, wherein said histidine is selected from the group comprising: L-histidines, histamine dihydrocholoride, DL-histidine, D-histidine hydrochloride monohydrate, L-histidine hydrochloride mornohydrate, L-histidine menthyl ester dihydrochiloride, L-histidinol dihydrochioride and combinations thereof.

10. The composition of claim 7, wherein said histidine has a weight percent between about 0.001% up to about 1.0%.

11. The composition of claim 10, wherein said histidine has a weight percent between about 0.025% up to 0.10%.

12. The composition of claim 1, wherein said capsaicin is selected from the group: nordihydrocapsaicin, capsaicin, dihydrocapsaicin, homocapsaicin, and combinations thereof.

13. The composition as in claim 1 wherein said capsaicin is in the range of 0.0001% to 62% by weight of capsaicin.

14. The composition of claim 13, wherein said capsaicin is in the range of 0.025 to 20 wt. %.

15. The composition of claim 14, wherein said capsaicin is in the range of 0.025 to 2 wt %.

16. The composition as in claim 15, wherein said capsaicin is in the range of 0.025% to 0.25% by weight.

17. The composition as in claim 1, wherein said ester is between 0.10 wt. % and 1.0wt. %.

18. The composition as in claim 1, wherein said ester is menthyl lauryl adequate to achieve 0.1 to 16 wt. % menthol in the formulation.

19. The composition of claim 17 wherein said ester is menthyl lauryl pidolate.

20. The composition of claim 1, wherein said light scattering element has a particle size of up to 100 microns in diameter.

21. The composition of claim 18, wherein said light scattering element has a particle size of between about 30 microns and about 60 microns in diameter.

22. The composition of claim 1, wherein said light scattering element is selected from the group: titanium dioxide, zinc oxide, and benzophenones, methoxy cinnamate, para amino benzoic acid, octyl dodecyl neopentanoate, aluminum stearate with titanium dioxide, aluminum oxide with titanium dioxide, and combinations thereof.

23. The composition of claim 1, further comprises an additional anti-itch agent which is a member of the group: The methyl sulphonyl methane, sodium bicarbonate, calamine, allantoin, kaolin, cortisone, anti-inflammatory steroids, anti-allergic steroids and derivatives or combinations thereof.

24. A patch for treating arthritis and neurological pains consisting of an elastomeric adhesive unit on which is disposed a formulation comprising;

a carrier;

a an encapsulated capsaicin;

an encapsulation agent for the capsaicin, wherein the encapsulation agent consists of a colloidal oatmeal or a dipotassium glycyrrhizinate;

a histidine;

lauryl menthyl esters of amino acid; and polysorbitol.

25. A gel comprising:

a carrier;

an encapsulated capsaicin;

an encapsulation agent for the capsaicin, wherein the encapsulation agent consists of a colloidal oatmeal or a dipotassium glycyrrhizinate;

lauryl menthyl esters of amino acid;

a light scattering element having a particle size up to 100 nm; and benzyl alcohol.

26. The gel of claim 25, further comprising a histidine.

27. A sunscreen comprising:

a carrier;

an encapsulated capsaicin;

an encapsulation agent for the capsaicin, wherein the encapsulation agent consists of a colloidal oatmeal or a dipotassium glycyrrhizinate;

lauryl menthyl esters of amino acid;

a light scattering element having a particle size up to 100 nm; and benzyl alcohol.

28. The sunscreen of claim 27, further comprising histidine.

29. A cream for treating pruritis comprising:

a carrier;

an encapsulated capsaicin;

an encapsulation agent for the capsaicin, wherein the encapsulation agent consists of a colloidal oatmeal or a dipotassium glycyrrhizinate;

lauryl menthyl esters of amino acid;

a light scattering element having a particle size up to 100 nm; and benzyl alcohol.

30. The cream of claim 29, further comprising histidine and polysorbitol.

31. A transdermal application comprising:

a carrier;

an encapsulated capsaicin;

an encapsulation agent for the capsaicin, wherein the encapsulation agent consists of a colloidal oatmeal or a dipotassium glycyrrhizinate;

lauryl menthyl esters of amino acid;

a light scattering element having a particle size up to 100 nm;

niacin;

histamine dicholoride; and polysorbitol.

32. The composition of claim 1, further comprising aloe.

33. The composition of claim 3, further comprising aloe.

* * * * *